United States Patent
Mistretta et al.

(10) Patent No.: US 10,002,445 B2
(45) Date of Patent: Jun. 19, 2018

(54) SYSTEM AND METHOD FOR RESOLVING ARTIFACTS IN FOUR-DIMENSIONAL ANGIOGRAPHIC DATA

(71) Applicant: Wisconsin Alumni Research Foundation, Madison, WI (US)

(72) Inventors: Charles A. Mistretta, Madison, WI (US); Michael A. Speidel, Madison, WI (US); Jordan Slagowski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 146 days.

(21) Appl. No.: 15/055,272

(22) Filed: Feb. 26, 2016

(65) Prior Publication Data

US 2017/0249758 A1 Aug. 31, 2017

(51) Int. Cl.
G06K 9/00 (2006.01)
G06T 11/00 (2006.01)
G06T 7/00 (2017.01)

(52) U.S. Cl.
CPC .......... *G06T 11/003* (2013.01); *G06T 7/0016* (2013.01); *G06T 2207/10076* (2013.01); *G06T 2207/10112* (2013.01); *G06T 2207/30101* (2013.01); *G06T 2211/404* (2013.01)

(58) Field of Classification Search
CPC .............. G06T 11/003; G06T 7/0016; G06T 2207/10076; G06T 2207/10112; G06T 2207/30101; G06T 2211/404
See application file for complete search history.

(56) References Cited

U.S. PATENT DOCUMENTS

| | | | |
|---|---|---|---|
| 8,634,620 B2 * | 1/2014 | Boese | A61B 5/7207 382/128 |
| 8,643,642 B2 | 2/2014 | Mistretta et al. | |
| 8,768,031 B2 | 7/2014 | Mistretta et al. | |
| 2008/0094396 A1 * | 4/2008 | Sabczynsdi | A61B 6/4441 345/424 |
| 2009/0105579 A1 * | 4/2009 | Garibaldi | A61B 1/00158 600/409 |
| 2012/0114217 A1 | 5/2012 | Mistretta et al. | |
| 2013/0046176 A1 | 2/2013 | Mistretta et al. | |
| 2014/0153690 A1 | 6/2014 | Claus et al. | |

(Continued)

OTHER PUBLICATIONS

Hermus, et al., Scatter Correction of Vessel Dropout Behind Highly Attenuating Structures in 4D-DSA, Proc. of SPIE, 2015, 9412:94124K-1 thru 94124K-7.

(Continued)

*Primary Examiner* — Shefali Goradia
(74) *Attorney, Agent, or Firm* — Quarles & Brady LLP

(57) ABSTRACT

A system and method are provided for medical imaging that includes acquiring, during a common imaging acquisition process, rotational, x-ray volume image data and x-ray tomosynthesis image data from a subject. The method includes reconstructing a time-resolved three-dimensional (3D) image volume from the rotational, x-ray volume image data and producing a four-dimensional (4D) image series of the subject with resolved overlapping features by selectively combining the time-resolved 3D image volume and the x-ray tomosynthesis imaging data.

24 Claims, 11 Drawing Sheets

(56) References Cited

U.S. PATENT DOCUMENTS

2017/0076467 A1    3/2017  Mistretta et al.

OTHER PUBLICATIONS

Royalty, 4D DSA: New Methods and Applications for 3D Time-Resolved Angiography for C-arm CT Interventional Imaging, Dissertation, Copyright by Kevin Royalty 2014.
Speidel, et al., Three-Dimensional Tracking of Cardiac Catheters Using an Inverse Geometry X-ray Fluoroscopy System, Med. Phys., 2010, 37(12):6377-6389.
PCT International Search Report and Written Opinion, PCT/US2017/019035, May 16, 2017.

* cited by examiner

SYSTEM AND METHOD FOR RESOLVING ARTIFACTS IN FOUR-DIMENSIONAL ANGIOGRAPHIC DATA

STATEMENT REGARDING FEDERALLY SPONSORED RESEARCH

This invention was made with government support under HL084022 and HL116567 awarded by the National Institutes of Health. The government has certain rights in the invention.

BACKGROUND

The present disclosure relates to x-ray angiography and, in particular, the disclosure relates to a system and method for resolving artifacts in time-resolved, three-dimensional (3D) angiographic images, referred to as four-dimensional (4D) angiographic x-ray data, such as may be caused by overlapping anatomical features.

Since the introduction of angiography beginning with the direct carotid artery punctures of Moniz in 1927, there have been ongoing attempts to develop angiographic techniques that provide diagnostic images of the vasculature, while simultaneously reducing the invasiveness associated with the procedure. In the late 1970's, a technique known as digital subtraction angiography (DSA) was developed based on real-time digital processing equipment. Due to steady advancements in both hardware and software, DSA can now provide depictions of the vasculature in both 2D and volumetric 3D formats. Three-dimensional digital subtraction angiography (3D-DSA) has become an important component in the diagnosis and management of people with a large variety of central nervous system vascular diseases as well as other vascular diseases throughout the body.

In recent years competition for traditional DSA has emerged in the form of computed tomography angiography (CTA) and magnetic resonance angiography (MRA). CTA is a less invasive technique but has lower spatial resolution. It is not time-resolved unless the imaging volume is severely limited. The images are not isotropic and secondary reconstruction yields degraded spatial resolution. CTA is also somewhat limited as a standalone diagnostic modality by artifacts caused by bone at the skull base and as well as the contamination of arterial images with opacified venous structures. Further, CTA provides no functionality for guiding or monitoring minimally-invasive endovascular interventions.

Significant advances have been made in both the spatial and the temporal resolution qualities of MRA. Currently, gadolinium-enhanced time-resolved MRA (TRICKS) is widely viewed as a dominant clinical standard for time-resolved MRA. TRICKS enables voxel sizes of about 10 mm$^3$ and a temporal resolution of approximately 10 seconds. Advancements such as HYBRID highly constrained projection reconstruction (HYPR) MRA techniques, which violate the Nyquist theorem by factors approaching 1000, can provide images with sub-millimeter isotropic resolution at frame times just under 1 second. Nonetheless, the spatial and temporal resolution of MRA are not adequate for all imaging situations and its costs are considerable. Furthermore, the spatial and temporal resolution is substantially below other methods, such as DSA.

The recently-introduced, four-dimensional (4D) DSA techniques can use rotational DSA C-arm imaging systems controlled with respect to a particular injection timing so that there is time dependence in the acquired reconstructed 4D volumes. As described in U.S. Pat. No. 8,643,642, which is incorporated herein by reference, a 3D DSA volume can be used as a constraining volume to generate a new 3D volume that contains the temporal information of each projection. As in 3D DSA, a mask rotation without contrast is followed by a second rotation during which contrast is injected. The process creates a series of time resolved 3D angiographic volumes that can be updated, for example, every $\frac{1}{30}$ of a second.

Thus, the above-described systems and methods have improved over time and, thereby, provided clinicians with an improving ability to visualize the anatomy of the vessels being studied. While 4D DSA techniques present a great advancement in the resources available to clinicians, 4D DSA images can include artifacts caused when anatomical features overlap in a 2D time frame x-ray projection. These artifacts can occur because the intensity information in overlapping anatomical features, at times, cannot be uniquely divided amongst the individual features. That is, existing 4D DSA methods reconstruct the 3D volume from the collection of 2D projections, and a time-resolved sequence of volumes is generated by back-projecting the information from the 2D frames onto the 3D volume. Overlapping anatomical features in a 2D projection, in some cases, cannot be perfectly distinguished and, thus, the intensity information cannot be attributed with confidence to individual features in the 3D volume. Thus, these overlapping features can cause uncertainty and inaccuracies in the 4D DSA reconstruction, which manifest as artifacts.

Therefore, it would be desirable to have systems and methods that are able create images, such as 4D DSA images, without artifacts caused by overlapping anatomical features.

SUMMARY

The present disclosure overcomes the aforementioned drawbacks by providing a system and method for generating and resolving overlapping structures in 4D DSA images using tomosynthesis image data. For example, the depth resolution of the tomosynthesis image data may be used to resolve overlap artifacts that could otherwise result in the 4D DSA images, without loss of temporal or spatial resolution.

In accordance with one aspect of the disclosure, a method for medical imaging is provided that includes acquiring, during a common imaging acquisition process, rotational, x-ray volume image data and x-ray tomosynthesis image data from a subject. The method also includes reconstructing a time-resolved three-dimensional (3D) image volume from the rotational, x-ray volume image data and producing a four-dimensional (4D) image series of the subject with resolved overlapping features by selectively combining the time-resolved 3D image volume and the x-ray tomosynthesis imaging data.

In accordance with another aspect of the disclosure, a system is provided for generating time resolved series of volume images including resolved overlapping features. The system includes an image processing system configured to receive image data acquired from a subject having received a dose of a contrast agent using an imaging system and determine tomographic volume data and tomosynthesis data from the image data acquired from the subject. The image processing system is also configured to process the tomographic volume data to generate three-dimensional (3D) volume images and, for a selected time frame in the 3D volume images, forward project through the 3D volume images using views from the tomosynthesis data corresponding to the selected time frame in the 3D volume images to create forward projected data. Using the tomosynthesis data, the image processing system reconstructs the forward projected data for the selected time frame to generate four-dimensional (4D) volume images with resolved overlapping features. The system also includes a display configured to display the 4D volume images with the resolved overlapping features.

In accordance with yet another aspect of the disclosure, a system is provided that includes an x-ray imaging system configured to rotate an x-ray source and x-ray detector through a range of view angles about a subject having received a dose of a contrast agent to acquire imaging data from the subject along at least a plurality of the range of view angles. The system also includes an image processing system configured to receive the image data to determine time-resolved, tomographic volume data and tomosynthesis imaging data, process the time-resolved, tomographic volume data to generate three-dimensional (3D) volume images, and, for a selected time frame in the 3D volume images, forward project through the 3D volume images using views from the tomosynthesis data corresponding to the selected time frame in the 3D volume images to create forward projected data. The image processing system is also configured to reconstruct the forward projected data for the selected time frame using the tomosynthesis data to generate four-dimensional (4D) volume images with resolved overlapping features. The system also includes a display configured to display the 4D volume images with the resolved overlapping features.

In accordance with another aspect of the disclosure, a method is provided for generating time-resolved series of volume data including resolved overlapping features. The method includes controlling a rotational x-ray imaging system to acquire time-resolved three-dimensional (3D) image volumes from a subject having received a dose of a contrast agent and controlling a scanning-beam digital x-ray (SBDX) imaging system to acquire tomosynthesis imaging data from the subject along a plurality of view angles included in the 3D image volumes. The method also includes producing a four-dimensional (4D) image series of the subject with resolved overlapping features by selectively combining the 3D image volumes and the tomosynthesis imaging data.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
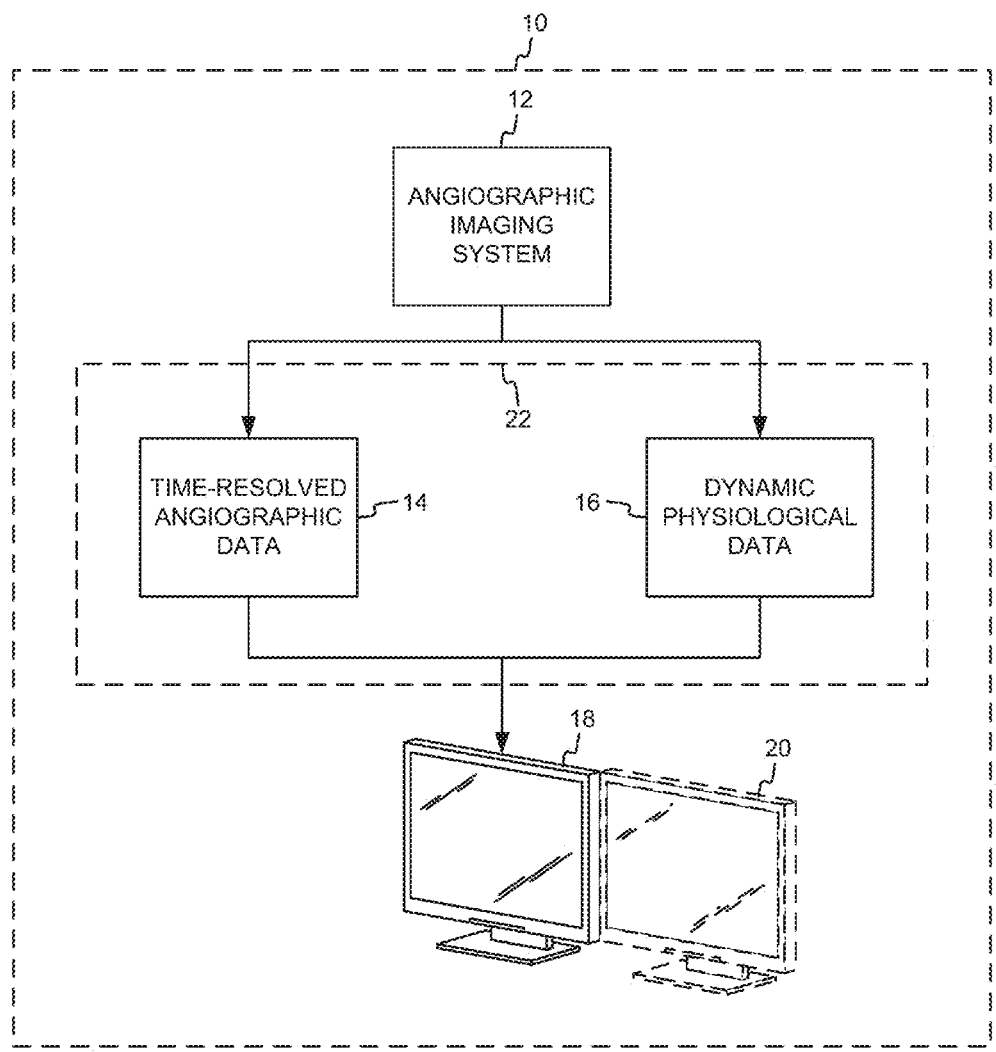
FIG. 1 is a block diagram of a system for creating time-resolved, three-dimensional (3D), volume images having resolved overlapping features in accordance with the present disclosure.

Referring to FIG. 1, a system 10 is illustrated for creating time-resolved angiographic images with improved visualization of overlapping features. In particular, the system 10 includes an angiographic imaging system 12. As will be described, the angiographic imaging system 12 can be used to acquire time-resolved angiographic data 14, which can include volumetric, tomographic image data and rapid, x-ray tomosynthesis image data. X-ray tomosynthesis image data is distinguished from other x-ray image data, such as volumetric, tomographic image data. For example, in conventional tomography, the x-ray source and detector move in synchrony on opposite sides of the region of interest to produce an imaging plane in sharp focus at the plane containing the rotational axis. However, structures above and below the plane aligned with the rotational axis are difficult to distinguish from those in the plane, particularly when the in-plane and out-of-plane structures are overlapping. On the other hand, tomosynthesis allows an arbitrary number of in-focus planes to be generated retrospectively from a sequence of projections that are acquired as an x-ray focal spot moves through a range of positions. As will be described, the systems and methods of the present disclosure combine rotational, volumetric, image acquisition capabilities of rotational, geometric tomography with the multiplane focusing capabilities of tomosynthesis to resolve overlapping structures within 4D DSA images.

Referring again to FIG. 1, optionally, the time-resolved angiographic data 14 can be combined with dynamic physiological data 16, such as described in co-pending U.S. application Ser. No. 14/855,209, entitled "System and Method For Determining Dynamic Physiological Information from Four-Dimensional Angiographic Data," which is incorporated herein by reference. The time-resolved angiographic data 14 can be processed and provided to a clinician via a display 18. As will be further described, the information may be provided to the clinician using multiple displays including a first display 18 and a secondary display 20 or multiple additional displays. As will also be described, the process of creating images from the time-resolved angiographic data 14 can be performed partially or in whole using an image processing system, which may include a graphics processing unit (GPU) or other processor, including a central processing unit (CPU), 22.

Figure 2A:
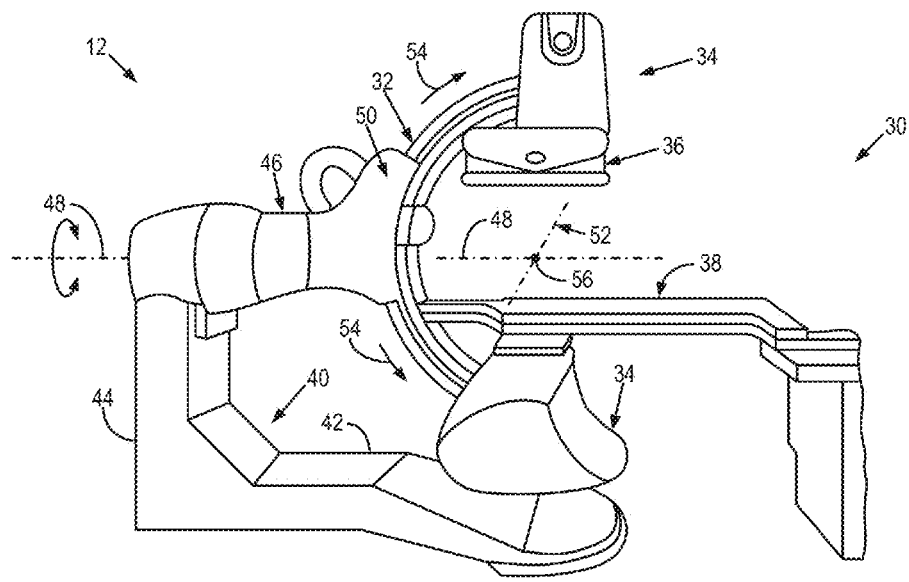
FIG. 2A is a perspective view of an example of an x-ray imaging system that can be used in accordance with the present disclosure to acquire imaging data.
Figure 2B:
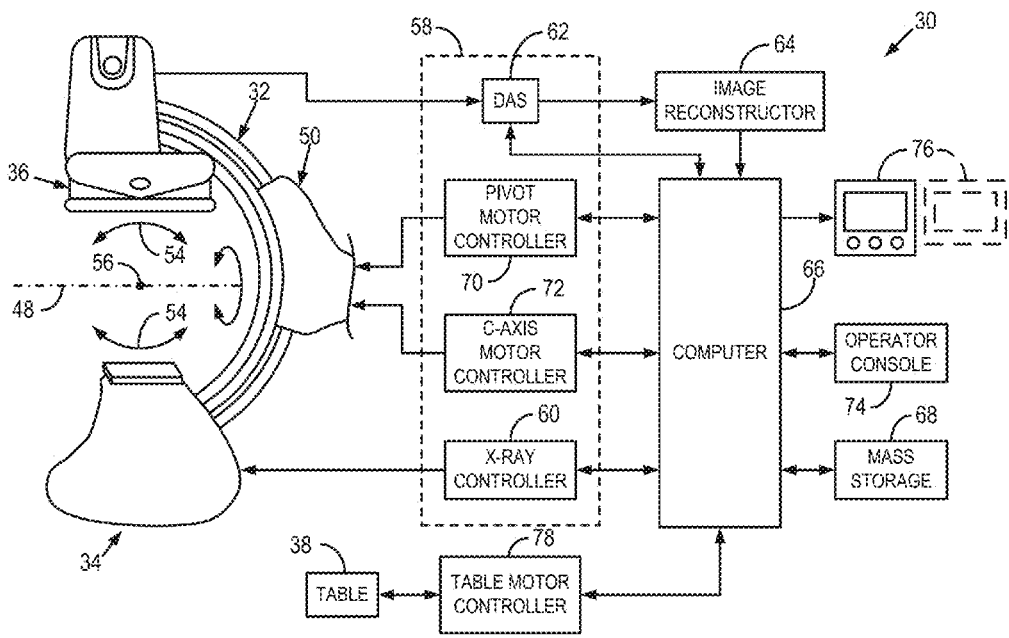
FIG. 2B is a block diagram of the system of FIG. 2A.

Referring now to FIGS. 2A and 2B, an example of the angiographic imaging system 12 may include an x-ray imaging system 30. The x-ray imaging system 30 is illustrated as a so-called "C-arm" imaging system; however, other geometries may be used to acquire 3D angiographic volume data and tomosynthesis imaging data. For example, any of a variety of x-ray imaging systems capable of acquiring data to create a 4D DSA image and acquire tomosynthesis images may be used. Furthermore, the x-ray imaging system 30 may be configured to perform as a 4D DSA imaging system, but is also configured to acquire x-ray tomosynthesis data and/or data bundled to form tomosynthesis data. For example, in one configuration, tomosynthesis data can be acquired using x-ray projections acquired as part of a conventional 4D DSA acquisition by selecting adjacent or proximate view angles to be "bundled" or used to create a dataset that is used as the tomosynthesis data that will be described. In another configuration, a rapid tomosynthesis system, such as a scanning-beam digital x-ray (SBDX) system can be used to acquire tomosynthesis data. Thus, the systems and methods described herein can be used with the above-described the C-arm x-ray system, a SBDX system, a bi-plane x-ray system, or other imaging systems. Thus, the systems described with respect to FIGS. 2A and 2B represent but one example of an imaging modality or system that can bused with the systems and methods of the present disclosure.

The imaging system 30 illustrated in FIGS. 2A and 2B, may be generally designed for use in connection with interventional procedures. The imaging system 30 is characterized by a gantry 32 forming a C-arm that carries an x-ray source assembly 34 on one of its ends and an x-ray detector array assembly 36 at its other end. As will be described, the x-ray source assembly 34 and the x-ray detector array assembly 36 may be designed to acquire both 3D image volume data and tomosynthesis imaging data. Regardless of the particular hardware configurations utilized, the gantry 32 enables the x-ray source assembly 34 and detector array assembly 36 to be oriented in different positions and angles around a patient disposed on a table 38, while enabling a physician access to the patient.

The gantry includes a support base 40, which may include a pedestal that has a horizontal leg 42 that extends beneath the table 38 and a vertical leg 44 that extends upward at the end of the horizontal leg 42 that is spaced from of the table 38. A support arm 46 is rotatably fastened to the upper end of vertical leg 44 for rotation about a horizontal pivot axis 48. The pivot axis 48 is aligned with the centerline of the table 38 and the support arm 46 extends radially outward from the pivot axis 48 to support a drive assembly 50 on its outer end. The C-arm gantry 32 is slidably fastened to the drive assembly 50 and is coupled to a drive motor (not shown) that slides the C-arm gantry 32 to revolve it about a C-axis 52, as indicated by arrows 54. The pivot axis 48 and C-axis 52 intersect each other at an isocenter 56 that is located above the table 408 and they are perpendicular to each other.

The x-ray source assembly 34 is mounted to one end of the C-arm gantry 32 and the detector array assembly 36 is mounted to its other end. As will be discussed in more detail below, the x-ray source assembly 34 includes one or more focal spots (not shown in FIGS. 2A and 2B) that emit beam(s) of x-rays, which are directed at the detector array assembly 36 and which may include one or more detector systems (not shown in FIGS. 2A and 2B). Both assemblies 34 and 36 are arranged about the pivot axis 38 such that the center ray of this cone beam passes through the system isocenter 56. The center ray of any x-ray beam can, thus, be rotated about the system isocenter 56 around either the pivot axis 48, along the C-axis 52, or both during the acquisition of x-ray attenuation data from a subject placed on the table 38.

Referring particularly to FIG. 2B, the rotation of the assemblies 34 and 36 and the operation of the x-ray sources are governed by a control system 58 of the imaging system 30. The control system 58 includes an x-ray controller 60 that provides power and timing signals to the x-ray source. A data acquisition system (DAS) 62 in the control system 58 samples data from detector elements in the detector array assembly 36 and passes the data to an image reconstructor 64. As will be described, the image reconstructor 64 is configured to receive both 3D image volume data and tomosynthesis image data from the DAS 62 and performs image reconstruction that resolves overlapping features. The image reconstructed by the image reconstructor 64 is applied as an input to a computer 66, which stores the image in a mass storage device 68 or processes the image further.

The control system 58 also includes pivot motor controller 70 and a C-axis motor controller 72. In response to motion commands from the computer 66, the motor controllers 70 and 72 provide power to motors in the imaging system 30 that produce the rotations about the pivot axis 38 and C-axis 52, respectively. A program executed by the computer 66 generates motion commands to the motor controllers 70 and 72 to move the assemblies 34 and 36 in a prescribed scan path.

The computer 66 also receives commands and scanning parameters from an operator via a console 74 that has a keyboard and other manually operable controls. An associated display 76 or displays allows the operator to observe the reconstructed image and other data from the computer 66. The operator-supplied commands are used by the computer 66 under the direction of stored programs to provide control signals and information to the DAS 62, the x-ray controller 60, and the motor controllers 70 and 72. In addition, the computer 66 operates a table motor controller 78, which controls the patient table 38 to position the patient with respect to the system isocenter 56.

Figure 2C:
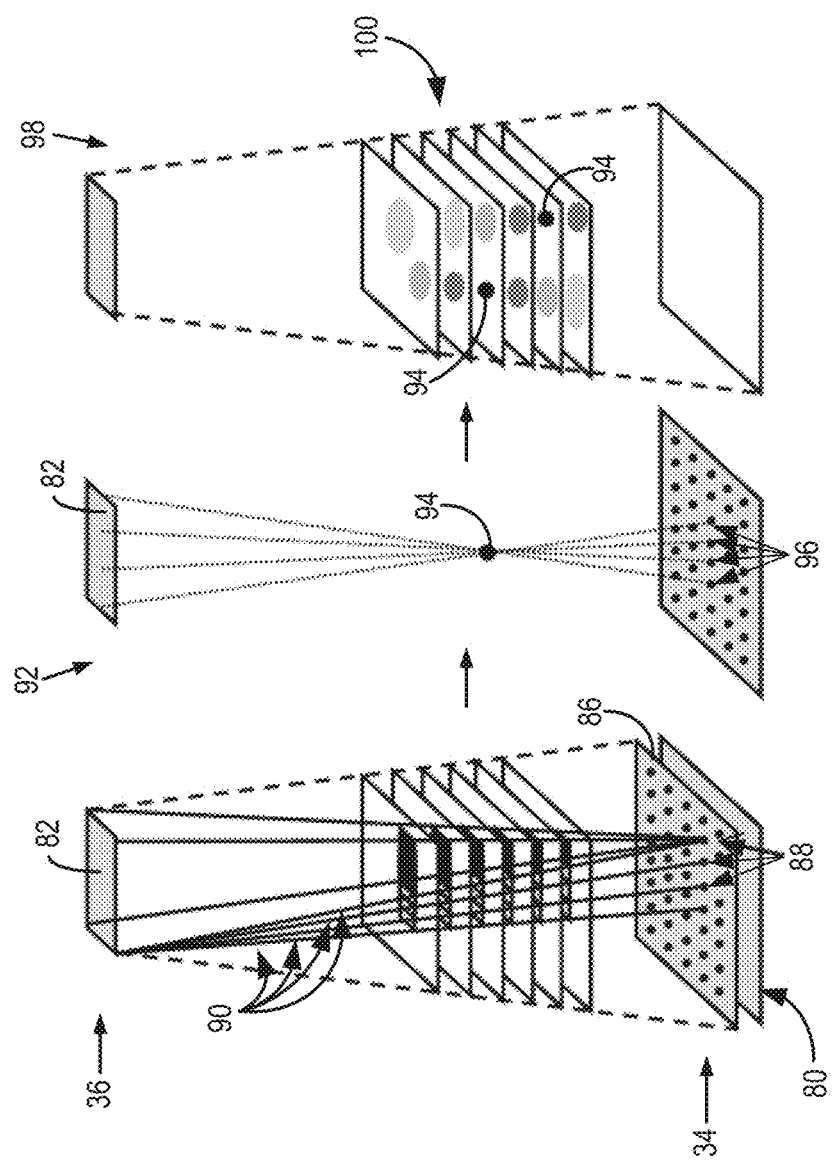
FIG. 2C is a graphic illustration of a data acquisition and reconstruction strategy for tomosynthesis data acquired in accordance with the present disclosure.

As mentioned above, the x-ray source assembly 34 contains one or more focal spots that emit one or more beams of x-rays when energized. In particular, as illustrated in FIG. 2C, the x-ray source assembly 34 may include an array of focal spot positions distributed on a surface 80 which are sequentially energized to generate a series of x-ray beams directed toward a detector array 82. The detector array 82 may include one or more photon counting detectors and/or two-dimensional flat panel digital detectors. In the case of photon counting detectors, individual counts are created for each photon captured by the detectors. On the other hand, for traditional energy integrating detectors, each detector element produces an electrical signal that represents the intensity of an impinging x-ray.

More particularly, regardless of the particular hardware included in the focal spot array 80 and the detector array 82, the focal spot array 80 and detector array 82 may be configured to acquire x-ray data that is capable of forming or being segregated into two forms of data. First, 3D, tomographic volume data may be acquired or formed from the acquired data. Second, tomosynthesis data may be acquired or formed from the acquired data. For example, the focal spot array 80 and detector array 82 may be configured to perform as a scanning-beam digital x-ray system to collect tomosynthesis data at each rotational angle or frame period and collect 3D, tomographic volume data as the focal spot array 80 and detector array 82 are rotated together through specific frame periods.

If the focal spot array 80 and detector array 82 may be configured to perform as a scanning-beam digital x-ray system, the focal spot positions are rapidly and sequentially energized by an electron beam. A multi-hole collimator 86 is used to create a series of projections 88 when the focal spot array 80 and detector array 82 are positioned at a given rotational angle or frame period to present an array of x-ray beams 90 at that given rotational angle. Accordingly, with the focal spot array 80 and detector array 82 at a given rotational angle defining a given frame period 92, a given point 94 in the field of view is imaged from a range of angles 96. Thus, during reconstruction 98, tomosynthesis images can be created as a stack of planes 100 where in-plane objects, such as the given point 94, appear sharp and out-of-plane objects are blurred out.

Figure 2D:
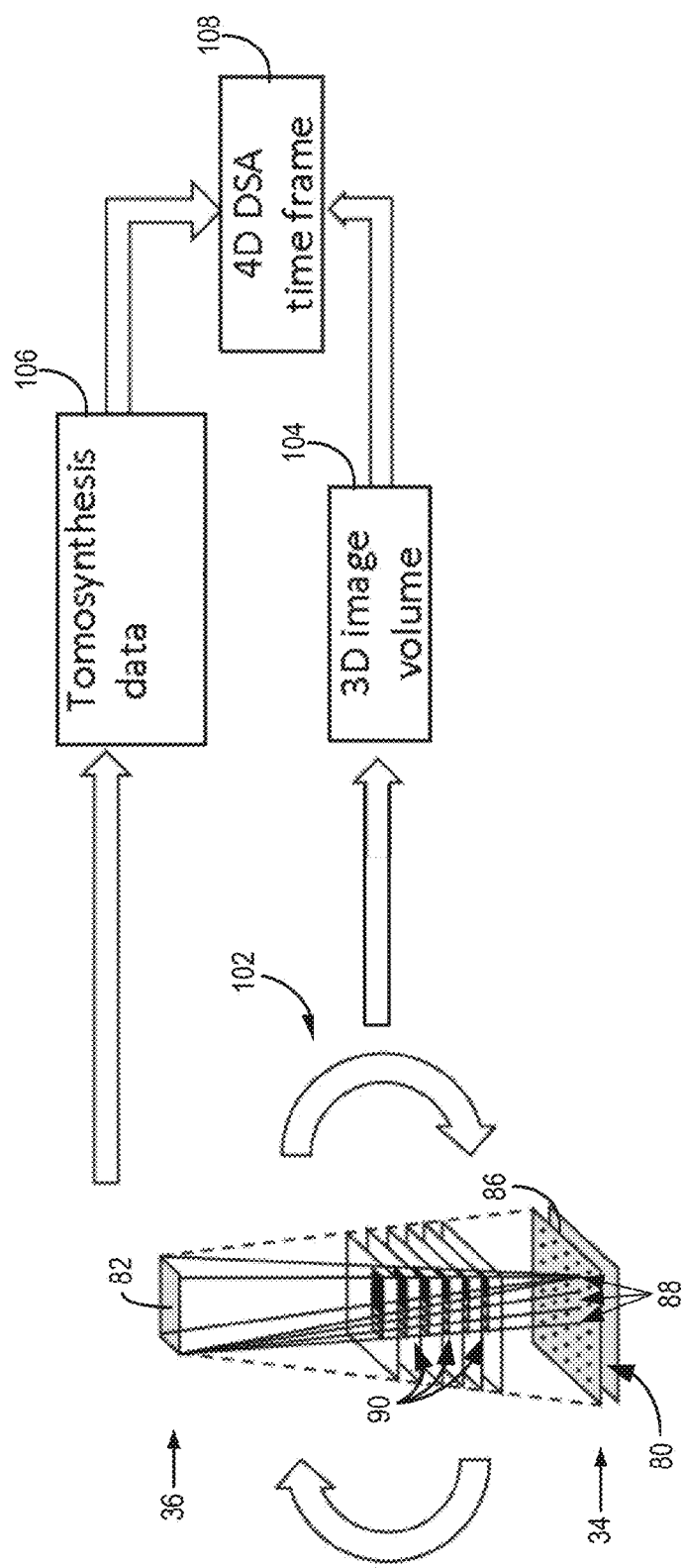
FIG. 2D is a graphic illustration of a data acquisition and image reconstruction strategy for creating 4D DSA images in accordance with the present disclosure.

Referring to FIG. 2D, during operation, the x-ray source assembly 34 and detector system 82 are rotated 102 through a plurality of rotational angles about the system isocenter to acquire both 3D image volume data 104 and tomosynthesis imaging data 106. In particular, the 3D image volume data 104 is acquired as the x-ray source assembly 34 and detector system 82 are rotated 102 and the tomosynthesis imaging data 106 is acquired for each different rotational angle/frame period. To acquire the tomosynthesis imaging data 106, the series of projections 88 can acquire, for example, 100×100 positions in a frame period (1/15 sec) at a fixed rotational or gantry angle. By rotating the gantry and acquiring tomosynthesis data at each of a plurality of gantry angles (e.g., slightly more than 180 degrees), a 3D image volume data 104 is also acquired.

Alternatively, if the source 34 and detector array 82 are not configured to perform as a scanning-beam digital x-ray system, imaging a given point 94 in the field of view from a range of angles 96 can be achieved by collecting data for given projection views of the 3D, volume data 104 are acquired at small variations between rotational angle. That is, data in the 3D, volume data 104 that was acquired at rotational angles of the x-ray source 34 and detector system 82 that are proximate in time and/or space may be collected or bundled to form the tomosynthesis data.

Regardless of the particular system utilized to acquire the 3D image volume data 104 and the tomosynthesis data 106, as will be further described, the tomosynthesis imaging data 106 can be used to resolve ambiguities caused by overlapping features in the 3D image volume data 104, such as overlapping vessels. That is, the tomosynthesis imaging data 106 and the 3D image volume data 104 can be used to create improved 4D DSA images 108 that overcome artifacts associated with overlapping features. In particular, the projection data from a single gantry angle can be used to modify the 3D volume and generate a 4D DSA time frame 108. The procedure is repeated for each gantry angle in the scan to generate the sequence of 4D DSA time frames 108.

Figure 3:
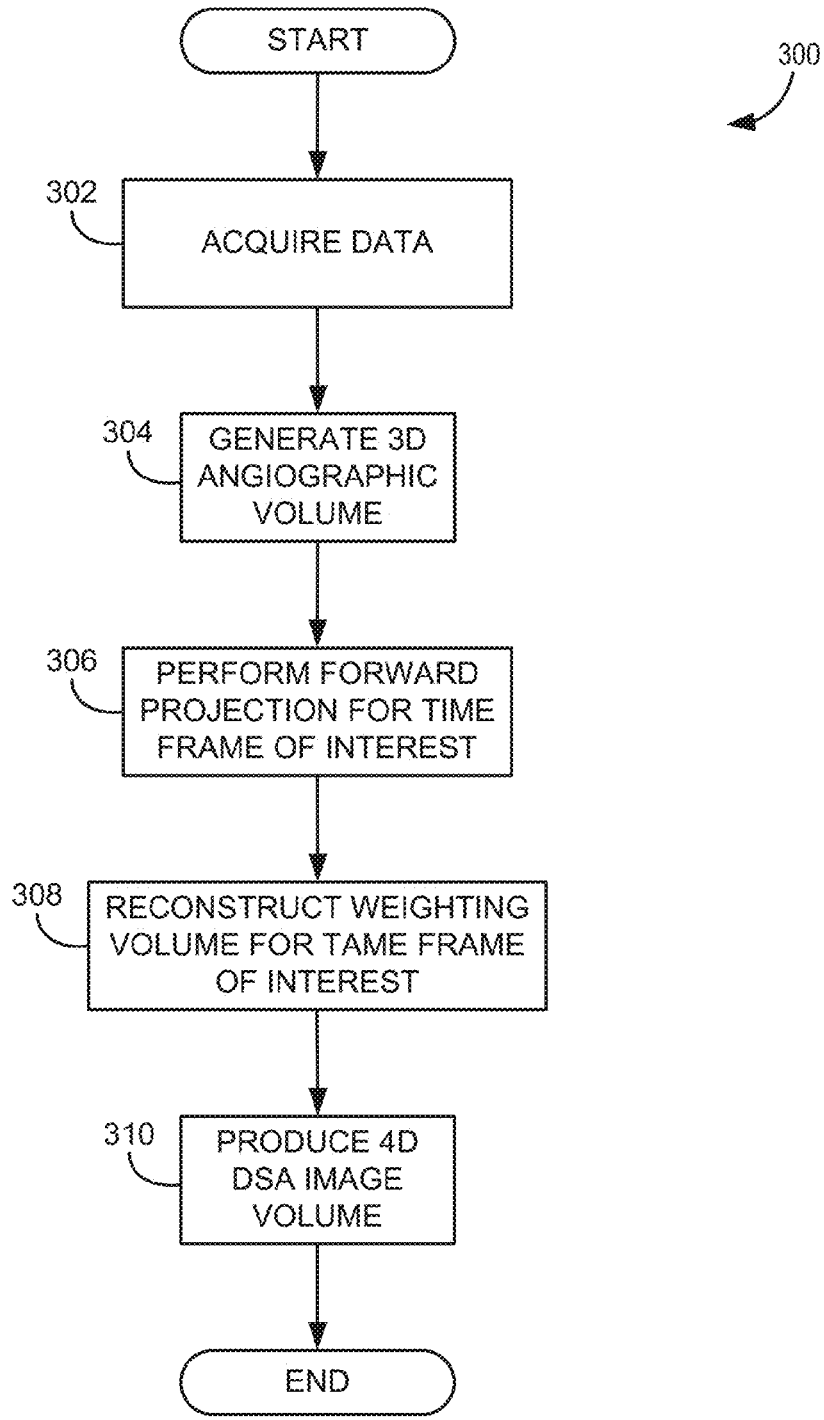
FIG. 3 is a flow chart setting forth examples of steps for producing a 4D DSA image having resolved overlapping features in accordance with the present disclosure.

More particular, referring to FIG. 3, the above-described system can be used to acquire or form both 3D image volume datasets and tomosynthesis datasets that can then be processed to generate a time-resolved 3D angiographic image in the form of a 4D DSA image. As will be described, the tomosynthesis projection data, which represents a subset of the projections acquired in a rotational DSA scan, can be used to resolve features, such as vessels, that would normally appear overlapped in the 4D DSA image volume. That is, the tomosynthesis projection data acquired for a given time frame contains ray measurements through each point in the patient volume which span a range of view angles, which, in turn, can be used to appropriately attribute intensity information across the 3D image volume to each respective overlapping feature.

Specifically, example steps of a process 300 for creating a 4D DSA image begins at process block 302 by performing one or more data acquisition(s) from a subject having received a dose of a contrast agent. The one or more data acquisition(s) are performed to create both a rotational, volumetric dataset and a tomosynthesis dataset.

At process block 304, a 3D angiographic volume is generated through application of iterative or analytical computed tomography (CT) reconstruction methods. Because, the rotational, volumetric dataset and the tomosynthesis dataset are performed together or substantially simultaneously, for each time frame of interest in the 3D angiographic volume, a matching set of x-ray tomosynthesis data is available. Thus, at process block 306, for each or many time frames of interest in the 3D volume, a numerical forward projection can be performed through the 3D volume for the selected time frame of the x-ray tomosynthesis geometry.

At process block 308 a weighting volume is formed for the selected time frame by normalization of the original tomosynthesis data from the time frame by the data produced by forward projection in process block 306. Then, at process block 310, the 3D angiographic volume generated at process block 304 is multiplied by the weighting volume created at process block 308 to produce a time-resolved 3D angiographic image volume, referred to as a 4D DSA image volume. The 4D DSA image volume is a 3D volume reflecting the image intensities that prevailed at the selected time frame.

Notably, U.S. Pat. No. 8,643,642, which is incorporated herein by reference in its entirety, describes various techniques for reconstructing 3D image volumes that may be used to perform a 4D DSA . Also, U.S. Pat. No. 8,768,031 is incorporated herein by reference in its entirety, which extends the 4D DSA imaging process to use time-independent 3D rotational DSA volumes. Furthermore, US Published Patent Application US2013/0046176, which describes the use of dual-energy x-ray imaging with 4D DSA, is incorporated herein by reference.

Figure 4:
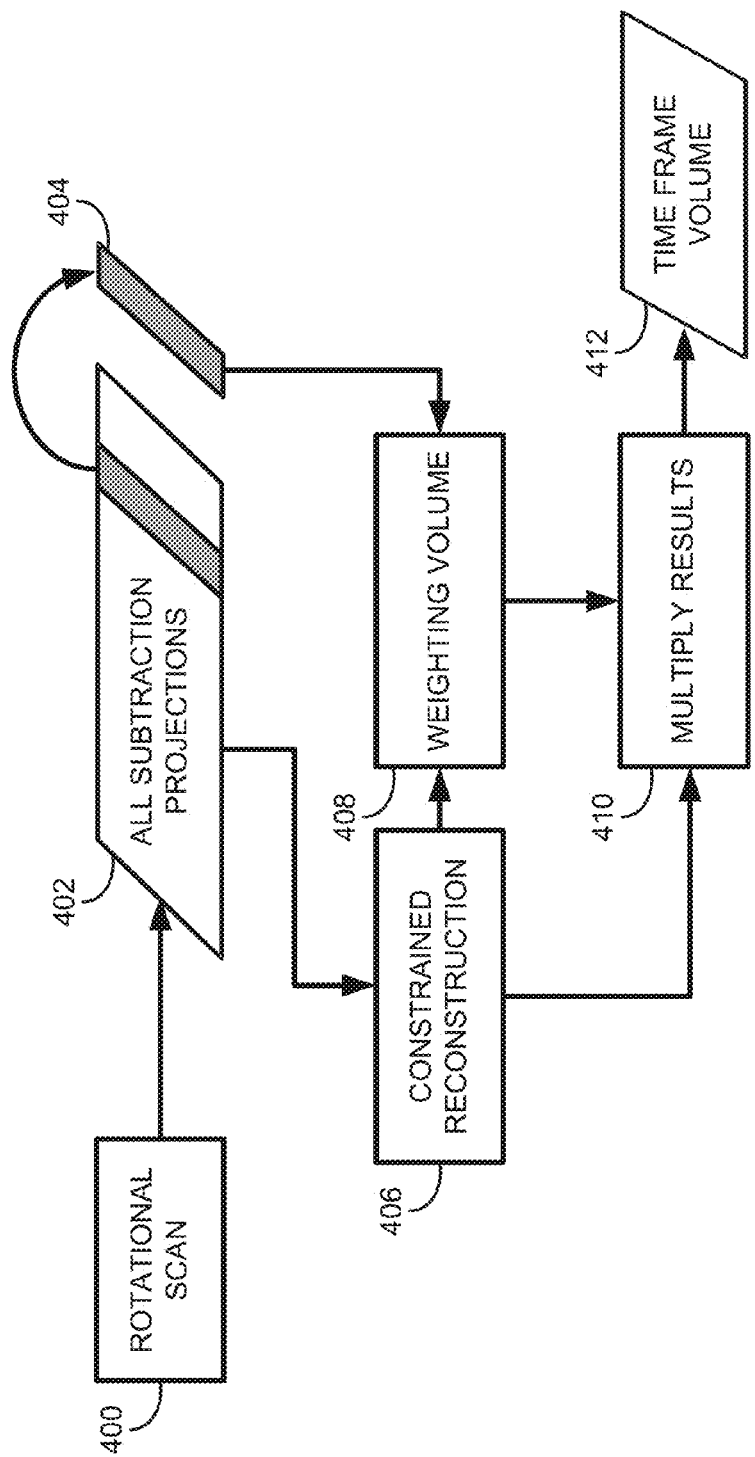
FIG. 4 is a flow chart setting forth a further example of creating a time frame volume in accordance with the present disclosure.

The process described in the above-cited documents can be generally described with reference to FIG. 4. That is, at process block 400 a rotational scan is performed that results in the creation of a plurality of projections 402 that spans a time period. That is, each projection corresponds to a given time, such that a given projection or set of data 404 is from a given time, t. As described above, a constrained reconstruction is performed at process block 406 and a weighting volume is created at process block 408. The results of these two reconstructions are multiplied at process block 410 to create a time frame volume 412. Mathematically, this can be represented as creating a 4D time frame volume, T(x,y,z,t), that is the product of a constrain volume, C(x,y,z), and weighting volume, W(x,y,z,t).

Figure 5A:
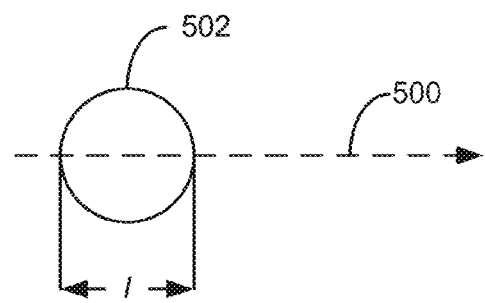
FIG. 5A is a graphic illustration of a ray passing through a vessel.

Referring now to FIG. 5A, an x-ray forming a ray 500 that passes through a vessel 502 of thickness "l" is illustrated. In this situation, the measured projection through the vessel 502 at time, t, along the ray 500 can be represented as $p_t=\mu_t l$. The vessel intensity in the reconstructed constrain volume can be represented as $C=\mu_c$. Now, forward projection of the constrain volume along the ray 500 is given by $p_c=\int \mu_c(x) dx = \mu_c l$. As such, the weighting is a ratio of projection values given by $$p_w = \frac{p_t}{p_c} = \frac{\mu_t l}{\mu_c l} = \frac{\mu_t}{\mu_c}.$$

The weight value along the ray 500 at the vessel 502 after backprojecting is given by $$W = p_w = \frac{\mu_t}{\mu_c}.$$

Thus, inside the vessel 502, the product of the constrain value and the weight value is $$T = CW = \mu_C \left(\frac{\mu_t}{\mu_C}\right) = \mu_t.$$

Figure 5B:
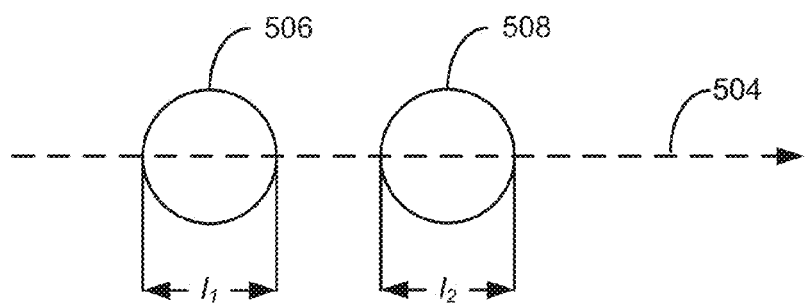
FIG. 5B is a graphic illustration of a ray passing through two vessels.
Figure 5C:
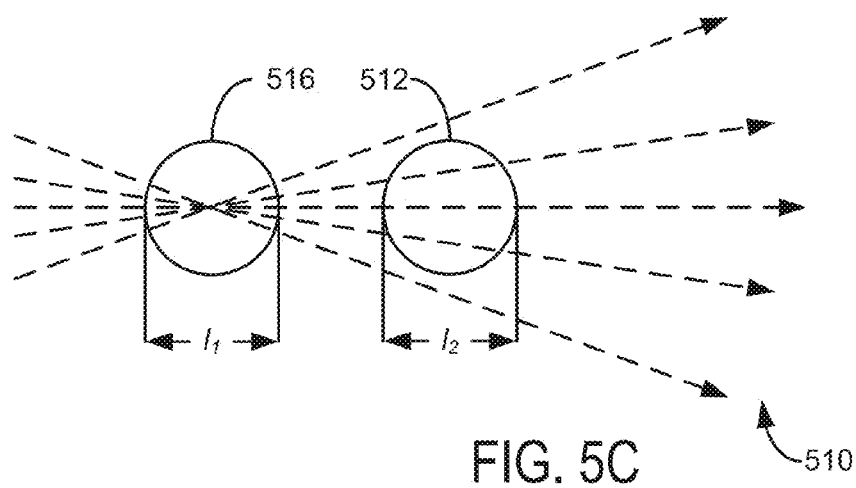
FIG. 5C is a graphic illustration of a series of tomographic rays passing through two vessels.

However, referring now to FIG. 5B, a ray 504 may pass through a first vessel 506 having thickness and a second vessel 508 having thickness $l_2$. In this case, the measured projection through the first vessel 506 at time, t, along the ray 504 can be represented as $p_t=\mu_{1t}l_1+\mu_{2t}l_2$. The intensity of the first vessel in the constrain volume can be represented as $C_1=\mu_{1c}$ and the intensity of the second vessel in the constrain volume can be represented as $C_2=\mu_{2c}$. Forward projection of the constrain volume along the ray 504 is given by $p_c=\int \mu_c (x)dx=\mu_{1c}l_1+\mu_{2c}l_2$. Using the same process as was used above for the first vessel, the product of the constrain value and the weight value would be $$T = CW = \mu_{1c}\left(\frac{\mu_{1t}l_1+\mu_{2t}l_2}{\mu_{1c}l_1+\mu_{2c}l_2}\right)$$

which is not the desired result. However, as described above, the acquisition or formation of tomsynthesis data at each time point can be used to reduce sensitivity to vessel overlap. That is, the present disclosure provides systems and methods that overcome challenges with resolving overlapping features, such as overlapping vessels in 4D DSA image volumes. For example, as illustrated in FIG. 5C, acquisition tomosynthesis data, with by leveraging a scanning beam x-ray system or proximate rotational view angles, results in a plurality of rays 510 that, for a given time frame or collected time frame, pass through each voxel position, such as one located in a first vessel 516. In this case, given the slight differences in view angle between each ray in the plurality of rays 510, not all rays pass through a second vessel 512 or reflect a common thickness of the vessel 512. As will be described, each voxel position can be projected and summed at multiple weights, while ignoring or otherwise reducing the influence of overlapped rays. As will be described, since there are multiple weights applied to each voxel, a normalization may be applied to each voxel in the weighting volume.

Figure 6A:
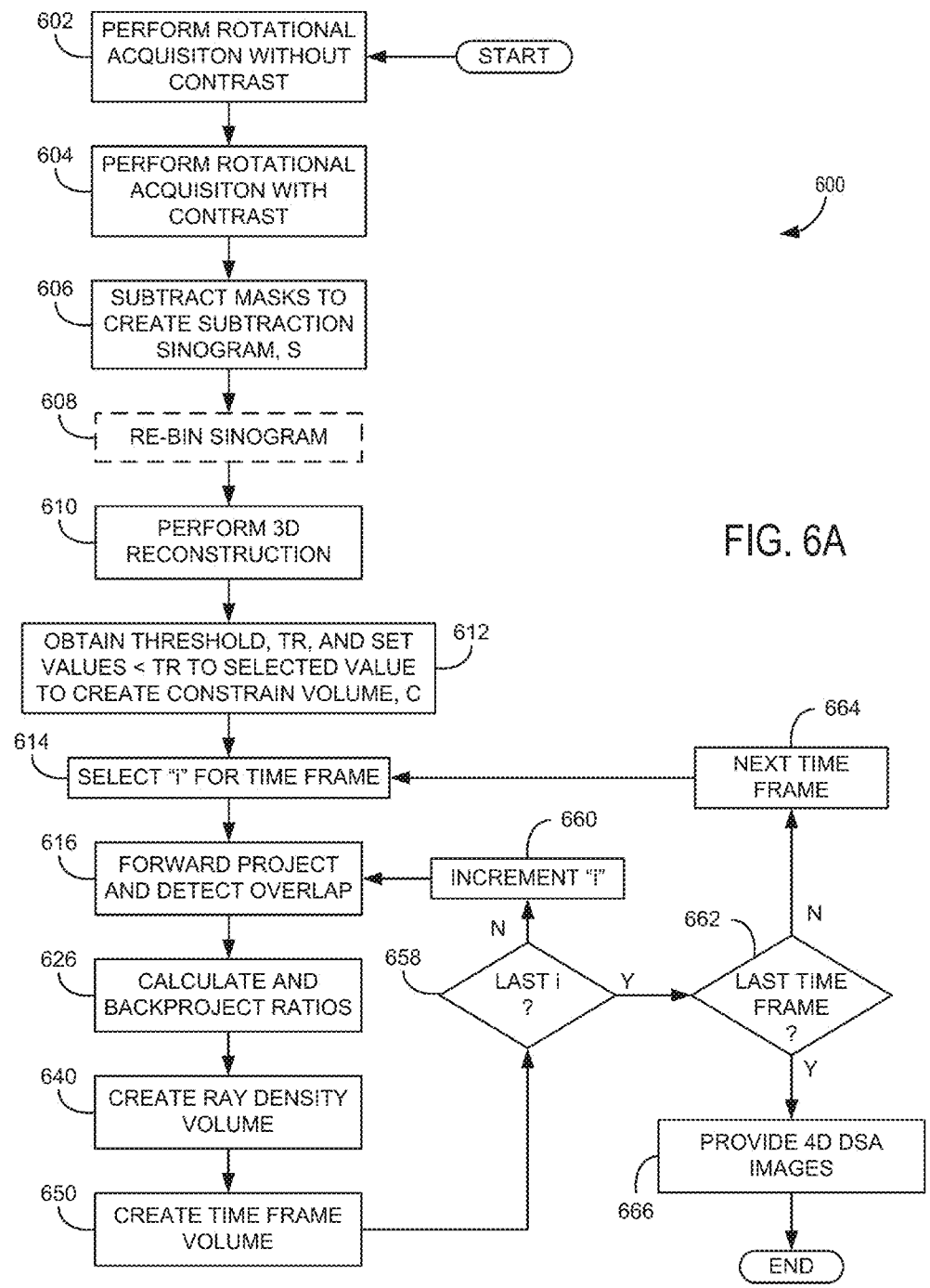
FIG. 6A is a flow chart setting forth examples of steps for creating time frame volumes or 4D DSA images in accordance with the present disclosure.

Thus, a more-specific example process 600 of the general process described above with respect to FIG. 3 is provided in FIG. 6A. The process 600 begins at process block 602 with the acquisition of data without contrast and at process block 604 with the acquisition of data after administration of a contrast agent. A mask sinogram can be created from the data acquired at process block 602 and a fill sinogram can be created from the data acquired at process block 604.

More particularly, as described above with respect to FIGS. 2A through 2D, the data is acquired at least using a rotational acquisition. For example, each rotational acquisition using the above-described C-arm can be a short scan, such as a scan over 200 degrees at 20 degrees per second. The data acquired at process block 602 and 604 are sinograms stored as data arrays representing measurements for each ray, as described above. To this end, each ray is associated with a specific combination of focal spot position, detector element position, C-arm angle, and time of acquisition.

At process block 606, the above-described mask sinogram and the fill sinogram are subtracted, such as using a log subtraction, to create a subtraction sinogram, S. At process block 608, the subtraction sinogram, S, may optionally be re-binned to reduce noise and/or simulate data acquired using parallel ray geometries.

At process block 610, a 3D reconstruction is performed to form a 3D DSA volume. Using this reconstructed volume, at process block 612, a constrain threshold, TR, is selected. The constrain threshold, TR, for example may be selected manually or derived. Once the constrain threshold, TR, is selected, values less than the constrain threshold, TR, may be set to a selected value, such as zero and the constrain volume, C, is created.

At process block 614 the rays which were collected within a specified time frame are identified and assigned indices, i. For example, as described above, if a scanning beam digital x-ray system is included in the source/detector system, the time frame is the period of a single tomosynthesis scan, such as described above with respect to FIG. 2C. On the other hand, if a scanning beam digital x-ray system is not available or included, the time frame may be defined as a series of proximately-acquired projection views that were acquired during the rotational acquisition. As described above, other imaging modalities/configurations can also be accommodated, such as bi-plane imaging systems and the like. In any case, at process block 614 a given ray of index "i" in a given time frame is selected.

Figure 6B:
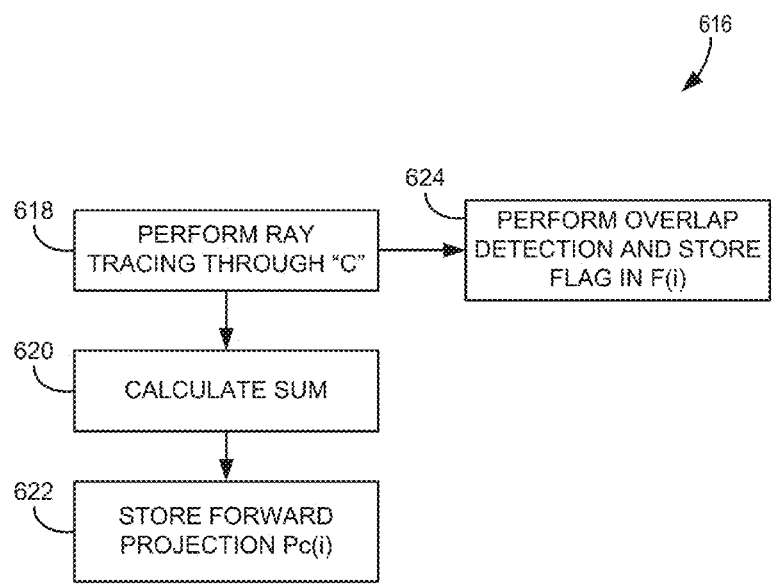
FIG. 6B is a further extension of the flow chart of FIG. 6A showing an example of a process for detecting overlaps.

At process block 616, forward projection and overlap detection is performed with respect to ray of index "i". For example, referring to FIG. 6B, one example process 616 for performing forward projection and overlap detection is illustrated. In this non-limiting example, at process block 618, ray tracing through the constrain volume, C, is performed to sample values along the ray. Ray tracing may be performed either in native ray geometry or in a re-binned ray geometry. At process block 620, these sample values along the ray are summed and the forward projection of the ray, Pc(i), is stored at process block 622. Also, at process block 624, overlap detection is performed and a flag, F(i), is set to indicate overlaps that are detected. For example, overlap may be detected by identifying multiple intensity transitions in the sampled values along the ray that are indicative of overlap. To this end, a threshold value may be selected that is indicative of the contrast change associated with a vessel. When reviewing the sample values along the ray, if multiple values are above the threshold value, an overlap has been detected. As illustrated, this ray processing method 616 may be performed in series or parallel.

Figure 7A:
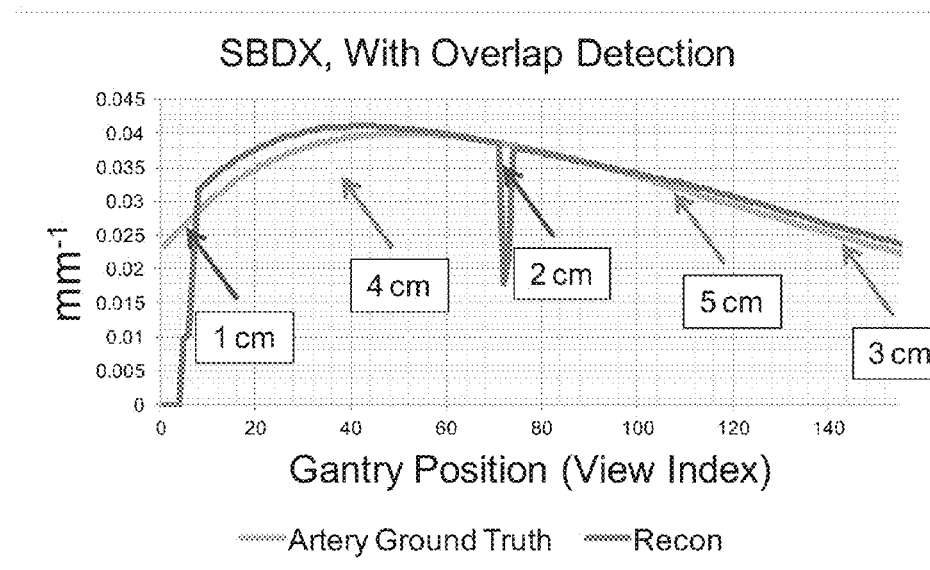
FIG. 7A is an experimental graph showing the influence of one overlap detection process.

As one non-limiting example, the flag may be stored as a "1" to indicate non-overlap or a "0" to indicate overlap. Additionally or alternatively, in some situations, it may be preferable to set the weight of the detected overlap to a value above "0." For example, the value may be set to "0.5" or, in some cases, "1." These other values may be used to reduce the severity of "dropout" artifacts caused by the overlap detection. Additionally or alternatively and with reference to FIG. 7A, the value selected may be influenced by the number of "good" rays sampling a given vessel, the separation between vessels, the tomographic angle used in the tomosynthesis data set, and the contrast of the vessel (e.g., the relative contrast of the vessel due to contrast agent arrival). For example, if two vessels are close together relative to a small tomographic angle and late in the contrast arrival curve, using overlap detection to set values to "0" may cause an undesirably large signal drop in the resulting images. This phenomenon is illustrated in FIG. 7A by the vessel located at a 2 cm distance from the other vessel. As can be seen in FIG. 7A, the confluence of small separation between vessels (2 cm), the tomographic angle used in the tomographic data, and the contrast of the vessel (e.g., the nearly-peak arrival of contrast to vessel), resulted in a "dropout" when the value was set to "0".

Figure 7B:
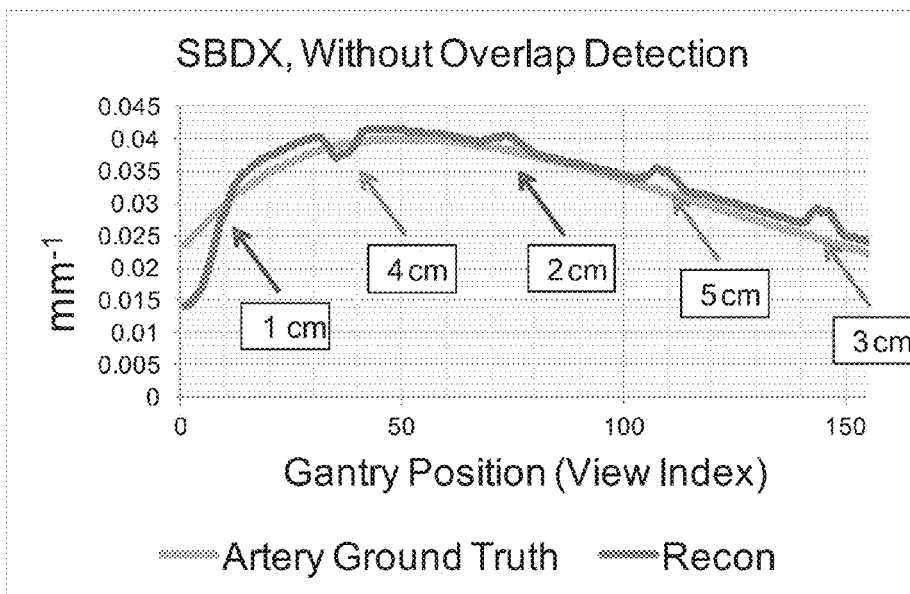
FIG. 7B is an experimental graph showing the influence of another overlap detection process.

When such a situation is identified, such as by using additional thresholds, it may be advantageous to set the value ray values to something greater than "0," such as "0.5" or even "1." As illustrated in FIG. 7B, such a process can be used to influence the potential dropout.

Figure 6C:
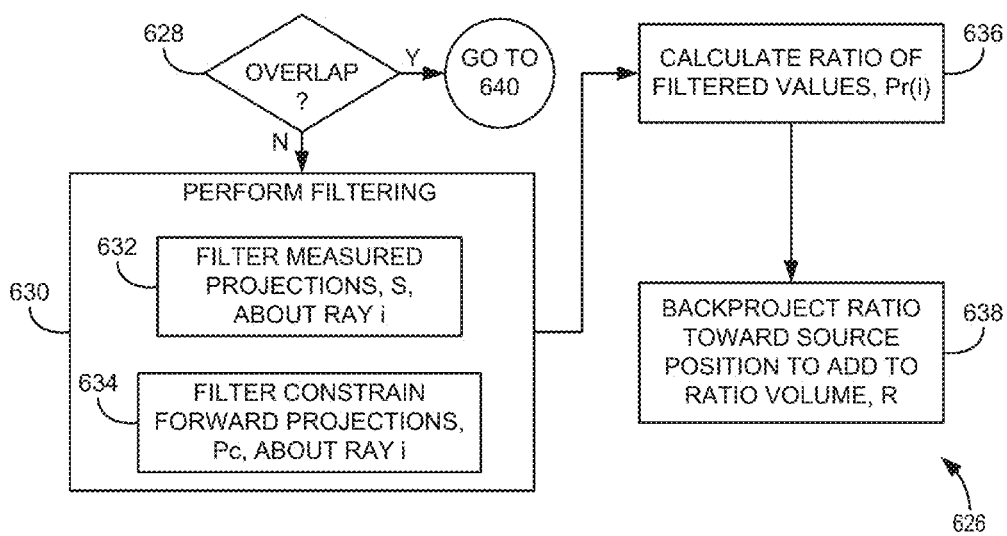
FIG. 6C is a further extension of the flow chart of FIG. 6A showing an example of a process creating backprojection ratios.

Referring again to FIG. 6A, following forward projection and overlap detection at process block 616, calculation and backprojection of ratios is performed at process block 626. For example, FIG. 6C provides one non-limiting example method of this process 626. The process 626 of FIG. 6C applies to identified overlaps. Thus, at decision block 628, a check is made to determine, for a given ray, whether an overlap was detected. If so, the process returns to FIG. 6A at process block 640, as will be described.

However, if an overlap is not detected in a given ray, the process continues from decision block 628 to process block 630 to perform filtering. To this end, the filtering of process block 630 may include filtering the measured projections in the subtraction sinogram S about ray i at process block 632. Also, at process block 634, the constrained forward projections, Pc(i), about ray i, may be filtered. That is, S and Pc are locally filtered, for example, using convolution or re-binning, on the rays corresponding to the current time frame. The subtraction sinogram S and the forward projections of the constrain volume Pc should be defined for the same geometry, native, or re-binned.

These filtered values are then used at process block 636 to create a ratio thereof, Pr(i). The ratio calculation may be modified to avoid division by zero or very-small values. At process block 638, this ratio is backprojected toward the source position to add to the ratio volume, "R". Thus, each voxel of the ratio volume, R, is a sum of backprojected ratios.

Figure 6D:
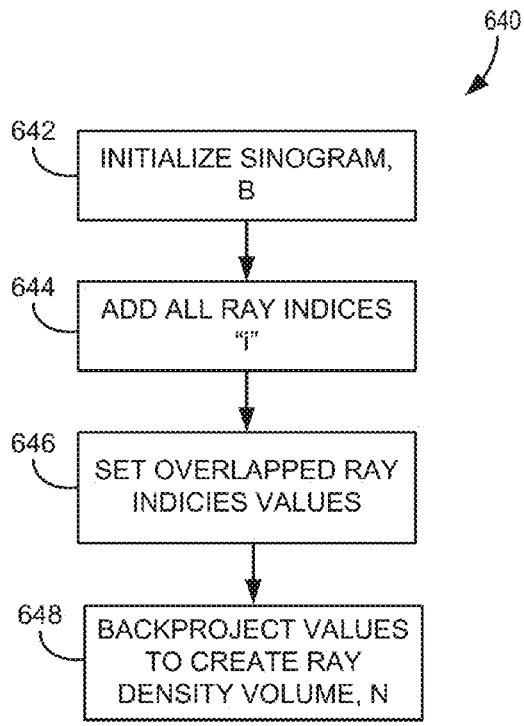
FIG. 6D is a further extension of the flow chart of FIG. 6A showing an example of a process for creating a ray density volume

Referring again to FIG. 6A, at process block 640 the process continues by creating the ray density volume, which is an image volume describing the number of non-overlapping rays passing through each voxel for the time frame of interest. More particularly, referring to FIG. 6D, one non-limiting example of a process 640 for creating the ray density volume is illustrated. In particular, the process 640 beings at process block 642 by initializing the sinogram. For example, an initial sinogram, B, may be created by setting all values to "0." Of course, other initialization values may be selected. At process block 644, for all ray indices, i, B may be set to "1." At process block 646, the overlap flags, F(i), are used to set values of B back to 0 for all overlapped ray indices. Finally, at process block 648, the values of B are backprojected to create a ray density volume, N.

Figure 6E:
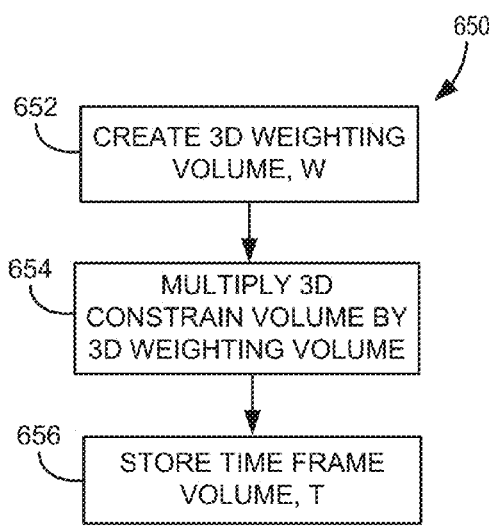
FIG. 6E is a further extension of the flow chart of FIG. 6A showing an example of a process for creating a portion of a time frame volume.

Referring to FIG. 6A, the ray density volume, N, and the 3D ratio volume, R, are used at process block 650 to create a time frame volume. More particularly, referring to FIG. 6E, at process block 652, a 3D weighting volume, W, is created. As a non-limiting example, to create the 3D weighting volume, W, the 3D ratio volume, R, is divided at process block 652 by the ray density volume, N, at all positions of non-zero values in N. As such, the ratio volume is normalized. Then, at process block 654, the 3D constrain volume, C, is multiplied by the 3D weighting volume, W. As such, a time frame volume, T, is created, which is stored at process block 656.

Referring again to FIG. 6A again, with a portion of the time frame volume, T, created, a check is made at decision block 658 to determine if the current "i" is the last for the given time frame. If not, "i" is incremented and steps 616 through 650 of FIG. 6A are repeated. If it is the last "i," a check is made at decision block 662 to determine if the current time frame is the last that was acquired. If not, at process block 664, the next time frame is selected at steps 614 through 662 of FIG. 6A are repeated. If it was the last time frame, reconstruction is complete and delivered at process block 666 as 4D DSA images.

The x-ray tomosynthesis data can be acquired using a variety of techniques. In one configuration, linear tomosynthesis can be performed using x-ray projections acquired in conventional 4D DSA. In this case, the "tomosynthesis data" is provided by selecting a series of projections centered on a time point of interest and acquired within some defined window of time. However, superior temporal resolution or superior depth resolution can be achieved with a rapid tomosynthesis system, such as a scanning-beam digital x-ray (SBDX) system.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for medical imaging comprising:
   acquiring, during a common imaging acquisition process, rotational, x-ray volume image data and x-ray tomosynthesis image data from a subject;
   reconstructing a time-resolved three-dimensional (3D) image volume from the rotational, x-ray volume image data;
   producing a four-dimensional (4D) image series of the subject with resolved overlapping features by selectively combining the time-resolved 3D image volume and the x-ray tomosynthesis imaging data.

2. The method of claim 1 wherein acquiring rotational, x-ray volume image data includes controlling a rotational x-ray imaging system to acquire the rotational, x-ray volume image data from the subject.

3. The method of claim 1 wherein acquiring the x-ray tomosynthesis image data includes controlling a scanning-beam digital x-ray (SBDX) imaging system to acquire the x-ray tomosynthesis imaging data from the subject along a plurality of view angles included in the rotational, x-ray volume image data.

4. The method of claim 3 wherein controlling the SBDX imaging system includes scanning an electron bean over an array of focal spot positions to acquire a series of projections for the plurality of view angles.

5. The method of claim 1 further comprising, for a selected time frame in the 3D image volume, forward projecting through the 3D image volume using views from the tomosynthesis image data corresponding to the selected time frame in the time-resolved 3D image volume to create forward projected data.

6. The method of claim 5 further comprising, using the tomosynthesis image data, reconstructing the forward projected data for the selected time frame.

7. The method of claim 6 further comprising normalizing the x-ray tomosynthesis image data using the forward projected data to create a normalized stack of planes and generating the 4D image series using the time-resolved 3D image volume and the normalized stack of planes.

8. The method of claim 1 wherein producing the 4D image series further includes detecting overlaps of features for each of a plurality of rays using the x-ray tomosynthesis imaging data and weighting data associated with rays for which overlap was detected to resolve the overlapping features.

9. The method of claim 1 further comprising performing an overlapping detection process to determine rays within the 3D image volume that extend through multiple vessels in the subject.

10. The method of claim 9 further comprising weighting rays within the 3D image volume that extend through multiple vessels in the subject to control against artifacts in the 4D image series created by the ray extending through multiple vessels.

11. A system for generating time resolved series of volume images including resolved overlapping features, the system comprising:
an image processing system configured to:
receive image data acquired from a subject having received a dose of a contrast agent using an imaging system;
determine tomographic volume data and tomosynthesis data from the image data acquired from the subject;
process the tomographic volume data to generate three-dimensional (3D) volume images;
for a selected time frame in the 3D volume images, forward project through the 3D volume images using views from the tomosynthesis data corresponding to the selected time frame in the 3D volume images to create forward projected data;
using the tomosynthesis data, reconstruct the forward projected data for the selected time frame to generate four-dimensional (4D) volume images using the 3D volume images; and
a display configured to display the 4D volume images with the resolved overlapping features.

12. The system of claim 11 wherein the tomosynthesis data includes scanning-beam digital x-ray projection data.

13. The system of claim 11 wherein the 4D volume images forms 4D digital subtraction angiography (DSA) data.

14. The system of claim 11 wherein the image processing system is further configured to analyze the image data to identify rays that were acquired from a tomographic angle within a selected range relative to a selected portion of the subject to form the tomsynthesis data.

15. The system of claim 11 wherein the image processing system is further configured to identify image data acquired using a scanning-beam digital x-ray (SBDX) imaging system to determine the tomosynthesis imaging data.

16. A system comprising:
an x-ray imaging system configured to rotate an x-ray source and x-ray detector through a range of view angles about a subject having received a dose of a contrast agent to acquire imaging data from the subject along at least a plurality of the range of view angles;
an image processing system configured to:
receive the image data to determine time-resolved, tomographic volume data and tomosynthesis imaging data;
process the time-resolved, tomographic volume data to generate three-dimensional (3D) volume images;
for a selected time frame in the 3D volume images, forward project through the 3D volume images using views from the tomosynthesis data corresponding to the selected time frame in the 3D volume images to create forward projected data;
using the tomosynthesis data, reconstruct the forward projected data for the selected time frame to generate four-dimensional (4D) volume images using the 3D volume images; and
a display configured to display the 4D volume images with the resolved overlapping features.

17. The system of claim 16 wherein the x-ray imaging system is configured to control a scanning-beam digital x-ray (SBDX) imaging system to acquire the tomosynthesis imaging data.

18. The system of claim 16 wherein the x-ray imaging system is configured to scan an electron beam over an array of focal spot positions to capture a series of projections for each of the plurality of the range of view angles.

19. A method for generating time-resolved series of volume data including resolved overlapping features, the method comprising:
controlling a rotational x-ray imaging system to acquire time-resolved three-dimensional (3D) image volumes from a subject having received a dose of a contrast agent;
controlling a scanning-beam digital x-ray (SBDX) imaging system to acquire tomosynthesis imaging data from the subject along a plurality of view angles included in the 3D image volumes; and
producing a four-dimensional (4D) image series of the subject with resolved overlapping features by selectively combining the 3D image volumes and the tomosynthesis imaging data.

20. The method of claim 19 wherein controlling the SBDX imaging system includes scanning an electron bean over an array of focal spot positions to acquire a series of projections for the plurality of view angles.

21. The method of claim 19 further comprising, processing the 3D image volumes to generate three-dimensional (3D) volume images and, for a selected time frame in the 3D volume images, forward projecting through the 3D volume images using views from the tomosynthesis imaging data corresponding to the selected time frame in the 3D volume images to create forward projected data.

22. The method of claim 21 further comprising, using the tomosynthesis imaging data, reconstructing the forward projected data for the selected time frame.

23. The method of claim 22 further comprising normalizing the tomosynthesis imaging data using the forward projected data to create a normalized stack of planes and generating the 4D image series using the 3D volume images and the normalized stack of planes.

24. The method of claim 21 wherein producing the 4D image series further includes detecting overlaps of features for each of a plurality of rays using the x-ray tomosynthesis imaging data and weighting data associated with rays for which overlap was detected to resolve the overlapping features.

\* \* \* \* \*

UNITED STATES PATENT AND TRADEMARK OFFICE
CERTIFICATE OF CORRECTION

PATENT NO. : 10,002,445 B2
APPLICATION NO. : 15/055272
DATED : June 19, 2018
INVENTOR(S) : Charles A Mistretta et al.

Page 1 of 1

It is certified that error appears in the above-identified patent and that said Letters Patent is hereby corrected as shown below:

In the Specification

Column 1, Lines 8-11:
"This invention was made with government support under HL084022 and HL116567 awarded by the National Institutes of Health. The government has certain rights in the invention.".

Should be:
--This invention was made with government support under HL084022 awarded by the National Institutes of Health. The government has certain rights in the invention.--.

Signed and Sealed this
Twenty-eighth Day of May, 2019

Andrei Iancu
*Director of the United States Patent and Trademark Office*